US007368287B2

(12) United States Patent
Lotteau et al.

(10) Patent No.: US 7,368,287 B2
(45) Date of Patent: *May 6, 2008

(54) USE OF L-α-LYSOPHOSPHATIDYLCHOLINE TO OBTAIN THE DIFFERENTIATION OF MONOCYTES INTO MATURE DENDRITIC CELLS IN VITRO

(75) Inventors: Vincent Lotteau, Vourles (FR); Patrice Andre, Lyon (FR)

(73) Assignees: Biomerieux, Marcy l'Etoile (FR); Institut National de la Sante et de la Recherche Medicale, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/503,402

(22) PCT Filed: Mar. 7, 2003

(86) PCT No.: PCT/FR03/00741

§ 371 (c)(1),
(2), (4) Date: Nov. 1, 2004

(87) PCT Pub. No.: WO03/076602

PCT Pub. Date: Sep. 18, 2003

(65) Prior Publication Data

US 2005/0054095 A1 Mar. 10, 2005

(30) Foreign Application Priority Data

Mar. 11, 2002 (FR) .................................. 02 03499
Jan. 30, 2003 (FR) .................................. 03 01063

(51) Int. Cl.
*C12N 5/08* (2006.01)
(52) U.S. Cl. ...................................... 435/372; 435/355
(58) Field of Classification Search .................. None
See application file for complete search history.

(56) References Cited

U.S. PATENT DOCUMENTS

| 4,746,652 A | 5/1988 | Buckalew, Jr. et al. |
| 5,434,182 A | 7/1995 | Isaacs et al. |
| 2004/0219672 A1* | 11/2004 | Lotteau et al. ............... 435/377 |

FOREIGN PATENT DOCUMENTS

| WO | WO 98/57631 A1 | 12/1998 |
| WO | WO 03/006634 A2 | 1/2003 |

OTHER PUBLICATIONS

Perrin-Cocon et al, 2001, Oxidized LDL promotes mature dendritic cell transition from differentiating monocyte. J. Immunol. vol. 167: 3785-91.*
Frostegard et al., 1997, Platelet activating factor and oxidized LDL induce immune activation by a common mechanims. Arter. Thromb., Vasc. Biol. vol. 17: 963-968.*
Labeur et al., 1999, Generation of tumor immunity by BM-DC correlates with dendritic cell maturation stage, J. Immunol., vol. 162: 168-175.*
Vuong et al. , 1999, Hypoalbuminemia incrases lysophsphatidylcholine in LDL of normocholesterolemic subjects. Kidney international, vol. 55: 1005-1010.*
Sigma Product information for L-a-lysophosphatidylcholine. 1998.*
Jeras et al., 2005, Transplant Immunology vol. 14: 231-244.*
Lyakh et al., 2005, J. Immunol. vol. 174: 2061-2070.*
Weber, Christian et al. "Enhancement of Monocyte Adhesion to Endotherial Cells by Oxidatively Modified Low-Density Lipoprotein is Mediated by Activation of CD11b" *Biochem. and Biophy. Rsrch Coms.* pp. 621-628 Jan. 17, 1995.
Dichmann, Stefan et al. "Downregulation of Platelet-Activing Factor Responsiveness During Maturation of Human Dendritic Cells." *Journal of Cellular Physiology* pp. 394-400 Jul. 10, 2000.
Kabarowski, Janusz H.S et al. "Lysophosphatidylcholine as a Ligand for the Immunoregulatory Receptor G2A." *Science* pp. 702-705 Jul. 27, 2001.
Carson, Monica J. et al. "The Push-Me Pull-You of T Cell Activation." *Science* pp. 618-619 Jul. 27, 2001.
Wanten. G. J. A. et al. "Influence of Structurally Different Lipid Emulsions on Human Neutrophil Oxygen Radical Production." *European Journal of Clinical Investigation* pp. 357-363 1999.
Beales, Philip E. et al. "Troglitazone Prevents Insulin Dependent Diabetes in the Non-Obese Diabetic Mouse." *European Journal of Pharmacology* pp. 221-225 1998.
Niino, Masaaki et a. "Amerliorization of Experimental Autoimmune Encephalomyelitis in C57BL/6 Mice by an Agonist of Peroxisome Proliferator-Activated Receptor-Y." *Journal of Neuroimmunology* pp. 40-48 2001.
S. Sozzani et al., "Human monocyte-derived and CD34+ cell-derived dendritic cells express functional receptors for platelet activating factor," *FEBS Letters*, vol. 418, No. 1-2, pp. 98-100, Nov. 1997.
F. Coutant et al., "Mature dendritic cell generation promoted by lysophosphatidylcholine," *Journal of Immunology*, vol. 169, No. 4, pp. 1688-1695, Aug. 2002.
D. Granato et al., "Effects of parenteral lipid emulsions with different fatty acid composition on immune cell functions in vitro," *Journal of Parental and Enteral Nutrition*, vol. 24, No. 2, pp. 113-118, Mar. 2000.

* cited by examiner

*Primary Examiner*—G. R. Ewoldt
*Assistant Examiner*—Amy Juedes
(74) *Attorney, Agent, or Firm*—Oliff & Berridge PLC

(57) ABSTRACT

The present invention relates to the use of L-α-lysophosphatidylcholine and/or an equivalent compound for the differentiation of monocytes into mature denditric cell.

Figure 1:
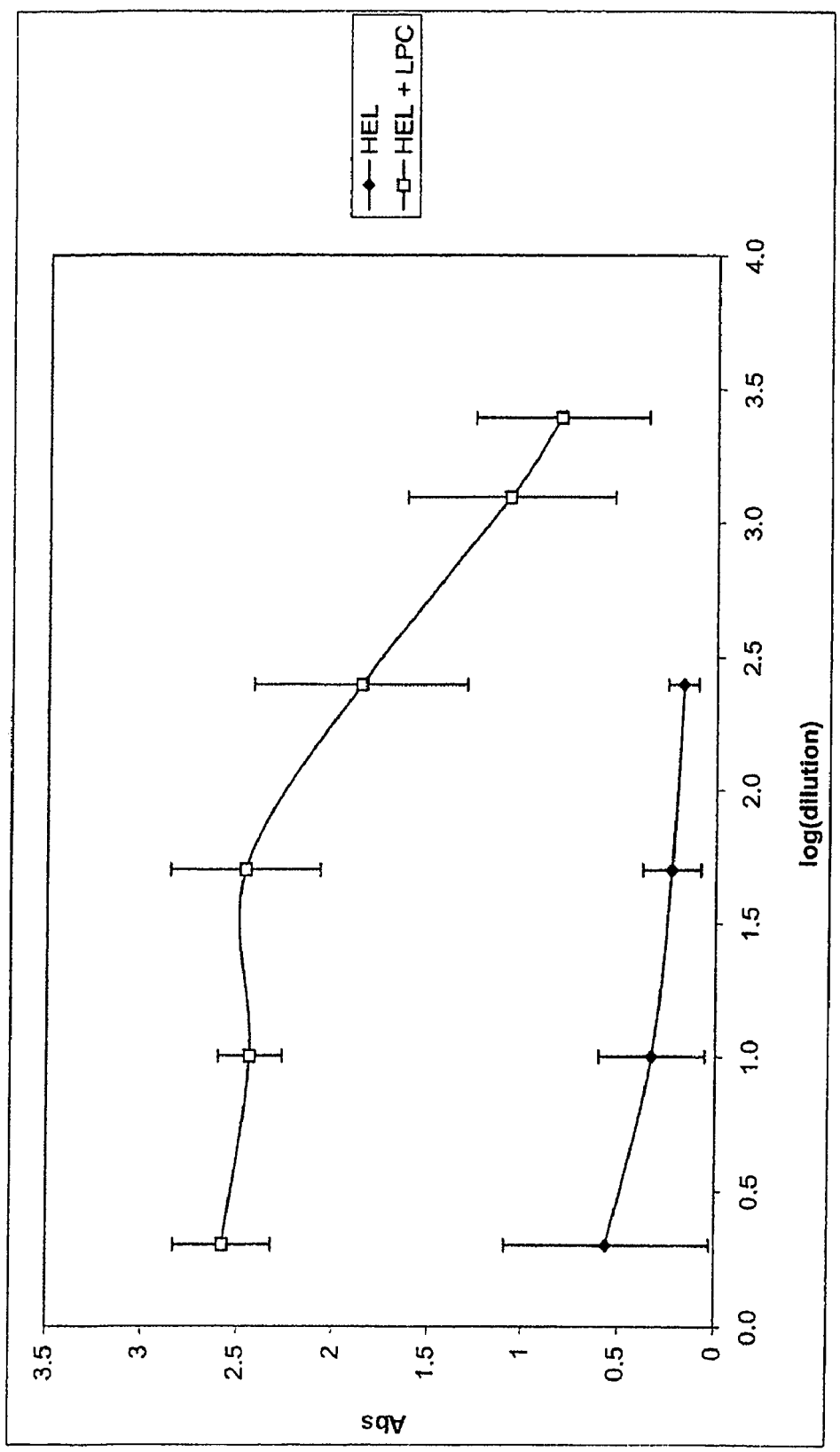

The present invention also relates to a method for differentiation monocytes into mature denditric cells according to which monocytes are provided in a medium suitable for their differentiation and L-α-lysophosphatidylcholine and/or an equivalent compound is added to said medium.

5 Claims, 1 Drawing Sheet

USE OF L-α-LYSOPHOSPHATIDYLCHOLINE TO OBTAIN THE DIFFERENTIATION OF MONOCYTES INTO MATURE DENDRITIC CELLS IN VITRO

The present invention relates to a method for differentiating monocytes into mature dendritic cells, according to which monocytes are provided in a suitable medium for their differentiation, and L-α-lysophosphatidylcholine is added to said medium. The present invention also relates to the use of at least one inhibitor of L-α-lysophosphatidylcholine, for producing a medicinal product for preventing an inflammation and/or for combating an inflammatory disease and/or an autoimmune disease.

Dendritic cells are involved in the development of an immune response and in the initiation of a specific T-lymphocyte response by recognition, uptake and presentation of antigens, in particular of infectious agents (Steinman et al. 1997, Immuno. Rev., 156: 25-37; Cella et al. 1997, Curr. Opin. Immunol., 9: 10-16). While immature dendritic cells take up and digest the antigens of infectious agents very effectively, certain signals, such as bacterial agents or inflammatory cytokines, can activate them by inducing a process of maturation, which is the initial step in triggering the adaptive immune response. In fact, during this activation, dendritic cells acquire the ability to migrate to lymphoid organs where T lymphocytes are found and the ability to transmit costimulation signals that are essential to the activation of naïve T lymphocytes. During this maturation, dendritic cells undergo functional and phenotypic modifications such as:
- an increase in surface molecules involved in the activation of T lymphocytes (such as CD40, CD80, CD83, CD86 and the molecules of the major histocompatibility complex (MHC) class I and class II),
- the production of proinflammatory cytokines (such as the interleukins IL-12, IL-1β, TNFα and IL-6),
- a decrease in their ability to take up and process the antigen.

By virtue of their abilities to develop an immune response and to initiate a specific T lymphocyte response, mature dendritic cells are of particular therapeutic interest, in particular in the fields of anti-infectious and antitumor immunization and of immunotherapy (Austin. 1998, Curr. Opin. Hematol. 5: 3-15; Reise Sousa et al. 1999, Curr. Opin. Immunol. 11: 392-399). These dendritic cells, by virtue of their ability to induce immuniotolerance, are also an advantageous target when it is desired to inhibit the immune response of a patient, in particular in order to combat autoimmune or inflammatory diseases.

In vitro, mature dendritic cells can be obtained from monocytes in culture. These monocytes are, in vivo, circulating cells which, when crossing in particular the vascular endothelial wall, come into contact with surrounding factors which influence their outcome in a manner which is still poorly understood. Schematically, three possibilities are then envisioned for these monocytes:
- exiting the tissues and returning to the lymph nodes,
- differentiating into macrophages
- differentiating into immature dendritic cells.

The first step for obtaining mature dendritic cells from monocytes in culture then consists in inducing the differentiation of the monocytes into immature dendritic cells with, in particular, the interleukin IL-4 and the factor GM-CSF (granulocyte macrophage-stimulating factor). After 6 days, 95% of the cells in culture are immature dendritic cells.

The second step then consists of induction of the maturation of the immature dendritic cells into mature dendritic cells using exogenous agents such as bacterial or viral agents. Thus, the KpOmpA protein from *Klebsiella pneumoniae* is capable of inducing the maturation of these immature dendritic cells into mature dendritic cells (P. Jeannin et al., Nature Immunology, 2000, 1: 502-509). Mention may also be made of the maturation of immature dendritic cells into mature dendritic cells by means of other exogenous molecules, such as bacterial membrane lipopolysaccharides (Dichman et al, Journal of Cellular Physiology, 2000, 185: 394-400). However, the use of exogenous molecules derived from infectious agents induces problems of safety and of cost (direct or indirect side effects in vivo; very important need for purification according to very strict legal or regulatory requirements, etc.), making the use of this type of molecule difficult in the context of vaccinology and of immunotherapy.

More recently, it has been described, by Perrin-Cocon et al., in 2001 (The Journal of Immunology, 167: 3785-3791), that the production of mature dendritic cells from monocytes undergoing differentiation can be induced with endogenous molecules, such as certain oxidized plasma lipoproteins, and more particularly oxidized low density lipoproteins (LDLs). However, oxidized LDLs are complex particles made up of proteins, triacyl glycerols, phospholipids, and free and esterified cholesterol, and are as a result difficult to synthesize artificially.

It is also important to note that, while stimulation of the differentiation of monocytes into dendritic cells is essential in certain therapeutic applications (during immunization, during stimulation of the immune response), it may also be essential to inhibit such a differentiation of monocytes into dendritic cells, or more generally to inhibit the maturation of immature dendritic cells, in other therapeutic applications, such as in an autoimmune or inflammatory disease. Treatments for combating inflammation, such as the taking of corticoids or the taking of aspirin, currently exist. The problem is that, when the inflammation is chronic, such treatments have side effects that are very harmful for the patient. The prolonged taking of corticoids can in particular engender a Cushing's syndrome during which demineralization, spontaneous fractures and diabetes are observed. The prolonged taking of aspirin can, for its part, engender stomach ulcers. The present invention proposes to solve the disadvantages of the state of the art by also proposing an anti-inflammatory molecule which is easy to synthesize and relatively inexpensive, and which inhibits the differentiation of monocytes into mature dendritic cells.

Thus, the present invention proposes to solve the disadvantages of the state of the art by providing a proinflammatory molecule, an endogenous molecule, which is easy to synthesize and relatively inexpensive and which stimulates the differentiation of monocytes into mature dendritic cells. The present invention also relates to the use of a lipid emulsion comprising triglycerides, phospholipids and glycerol, such as in particular INTRALIPID®, for inhibiting the differentiation of monocytes to mature dendritic cells, by virtue of a direct action, or an indirect action via inhibition of the action of L-α-lysophosphatidylcholine.

Surprisingly, the present invention relates to the use of L-α-lysophosphatidylcholine for differentiating monocytes into mature dendritic cells in vitro.

The term "L-α-lysophosphatidylcholine" is intended to mean a molecule for which the formula is as follows:

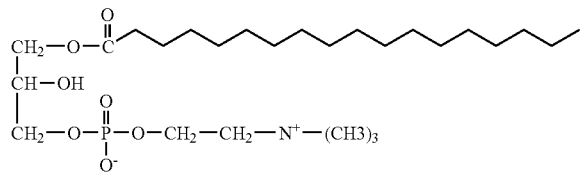

in which

represents a long chain of saturated fatty acids containing from 12 to 20 carbon atoms, preferably from 16 to 18.

In fact, one of the active molecules generated during LDL oxidation is L-α-lysophosphatidylcholine, hereinafter referred to as LPC. However, it has been shown that the binding of LPC to the G2A receptor, which is the high affinity receptor for LPC, inhibits in particular the proliferation and the activation of T lymphocytes, rather suggesting a role for LPC in inhibiting the triggering of an immune reaction (Carson & Lo, 2001, Science, 293: 618-619). In addition, it has also been shown that a high concentration of LPC (50 µM) inhibits the activity of the transcription factor NF-κB (nuclear factor κB), which is however known to be activated during the maturation of dendritic cells. In addition, LPC is present at high concentration in the plasma, suggesting that it is not active in the plasma, which would not predispose it to be chosen by those skilled in the art for therapeutic use.

The invention relates to a method for the differentiation in vitro of monocytes into mature dendritic cells, according to which:
A. monocytes are provided in a suitable culture medium,
B. the differentiation of the monocytes into dendritic cells is induced in the presence of a differentiation factor,
C. L-α-lysophosphatidylcholine is added to said medium and mature dendritic cells are obtained.

The expression "suitable culture medium" is intended to mean a medium comprising all the elements required for cell viability. By way of example, mention may be made of RPMI 1640 medium and its derivatives, and any culture medium well known to those skilled in the art. This medium comprises in particular at least one factor for differentiating monocytes into dendritic cells. The factors for differentiating monocytes into dendritic cells are well known to those skilled in the art, and mention may in particular be made of cytokines such as, without any implied limitation, the interleukin IL-4, the factor GM-CFS (granulocyte macrophage-stimulating factor), IL-13 or TNF (tumor necrosis factor).

In step C), the L-α-lysophosphatidylcholine is added in particular to said medium at a final concentration in the medium of between 10 and 80 µM, preferably between approximately 20 and 60 µM, and advantageously between 30 and 50 µM. Still in step C), the L-α-lysophosphatidylcholine is added to said medium between the 3rd and 6th day of monocyte differentiation, preferably between the 4th and 5th day of monocyte differentiation.

According to a particular embodiment of the invention, at least one biological agent is also added to the culture medium, in step C). The term "biological agent" is intended to mean a molecule (or a set of molecules) which is the target of an immune response or which allows the synthesis of this target. This biological agent can thus be chosen from bacterial, viral, yeast, parasite or fungal antigens, tumor antigens, and lysates of autologous and/or heterologous tumor cells. The term "autologous tumor cells" is intended to mean tumor cells belonging to the individual who receives a given medicinal product. The tumor cells can be obtained by taking a sample of cancerous tissue, in particular a biopsy or a surgical resection. The term "heterologous tumor cells " is intended to mean cells derived from tumors originating from an individual who is different from the one receiving a given medicinal product. The use of heterologous cells makes it possible in particular to obtain a medicinal product for treating patients suffering from cancer from whom it is not possible to obtain a tumor cell sample. This also makes it possible to use a standard source of tumor antigens. The term "cell lysate" is intended to mean a mixture of intracellular and/or membrane antigens, obtained by lysis of cells according to a protocol known to those skilled in the art, such as mechanical, chemical or enzymatic lysis. This biological agent may also be a nucleic acid which encodes at least one antigen chosen from bacterial, viral, yeast, parasite or fungal antigens, and tumor antigens. The term "tumor antigen" is intended to mean an antigen derived from tumor cells, such as a tumor-related peptide, in particular a peptide which interacts with class I molecules and which is presented to CD8 T lymphocytes. Mention may be made, in a known nonlimiting manner, of the following tumor antigens: MAGE-2, MAGE-3, MART, MUC-1, MUC-2, HER-2, GD2, carcinoembryonic antigen (CEA), TAG-72, ovarian-associated antigens OV-TL3 and MOV18, TUAN, alpha-fetoprotein (AEP), OFP, CA-125, CA-50, CA-19-9, renal tumor-associated antigen G250, EGP-40 (or EpCAM), S 100 (malignant melanoma-associated antigen), p53, prostate tumor-associated antigens (e.g. PSA and PSMA) and p21ras.

Thus, the addition of this biological agent to the culture medium makes it possible to obtain mature dendritic cells which then allow the activation of T lymphocytes which are directed against a given antigen. These mature dendritic cells, obtained in vitro, can then be reinjected in vivo.

In another embodiment of the invention, it is also possible to use, in step C, a compound equivalent to L-α-lysophosphatidylcholine, which is a molecule that acts according to the same cellular mechanisms of action as L-α-lysophosphatidylcholine, i.e. by the same membrane receptors, in particular G protein-coupled membrane receptors, such as the receptors G2A, GPR4 or the PAF (platelet activating factor) receptor, and/or via the same nuclear receptors, such as the PPAR receptors (peroxisome proliferator-activated receptor). This equivalent compound can thus in particular be an agonist for the abovementioned receptors (such as in particular O-methyl-PAF, carbamyl-PAF or 2-O-methyl-PAF), but also the PAF itself. This compound may also be a PPARδ agonist, such as in particular L165041 (Merck Research), GW-5015616 (Glaxo) or carboprostacylin (Cayman), or a PPARγ antagonist, such as in particular bisphenol A diglycidyl ethyl (Sigma) or DICLOFENAC® (2-[(2,6-dichlorophenyl)amino ]benzenacetic acid). This compound equivalent to L-α-lysophosphatidylcholine can be used alone or in synergy with L-α-lysophosphatidylcholine. According to a preferred embodiment of the invention, the L-α-lysophosphatidylcholine is used in synergy with platelet activating factor (PAF).

The invention also relates to a method for activating T lymphocytes in vitro, according to which:
A. monocytes are provided in a suitable culture medium, B. the differentiation of the monocytes into dendritic cells is induced in the presence of a differentiation factor,
C. L-α-lysophosphatidylcholine is added to said medium and mature dendritic cells are obtained,
D. a biological agent, as defined above, is added to said medium and the mature dendritic cells obtained in step B are directed against said biological agent,
E. the mature dendritic cells directed against the biological agent according to step C are brought into contact with T lymphocytes, and T lymphocytes directed against the biological agent are obtained.

Step C) can be carried out as described above. Such a method thus makes it possible to obtain, in vitro, T lymphocytes directed against a given biological agent, which can then be reinjected in vivo into a patient, in particular an immunodepressed patient.

The invention also relates to a method for maturing dendritic cells in vitro, according to which:
A. immature dendritic cells are provided in a suitable culture medium,
B. L-α-lysophosphatidylcholine is added to said medium and mature dendritic cells are obtained.

Those skilled in the art are well aware of dendritic cells and their various stages of maturation.

In step B), the L-α-lysophosphatidylcholine is added in particular to said medium at a final concentration in the medium of between approximately 10 and 80 µM, preferably between approximately 20 and 60 µmM, and advantageously between 30 and 50 µM. According to a particular embodiment of the invention, at least one biological agent as defined above is also added to the culture medium, in step B).

The invention also relates to a culture medium, characterized in that it comprises L-α-lysophosphatidylcholine and at least one differentiation factor as defined above.

In a preferred embodiment of the invention, L-α-lysophosphatidylcholine is at a final concentration in the medium of between approximately 10 and 80 µM, preferably between approximately 20 and 60 µM, and advantageously between 30 and 50 µM. According to a particular embodiment of the invention, the culture medium also comprises a biological agent as defined above, which is in particular a bacterial, viral, yeast, parasite or fungal antigen, an autologous and/or heterologous tumor cell lysate antigen, a tumor antigen, a nucleic acid which encodes a bacterial, viral, yeast, parasite or fungal antigen, or a nucleic acid which encodes a tumor antigen.

The invention also relates to the use of L-α-lysophosphatidylcholine as an agent for activating the immune system. The term "agent for activating" is intended to mean a molecule which, in a pharmaceutical composition, induces the effects of a medication or reinforces or completes the effects of the main medication. In the case of a vaccine composition, the L-α-lysophosphatidylcholine then plays the role of adjuvant which stimulates the host organism's immune response against a given antigen. Thus, the invention relates to a vaccine composition, characterized in that it comprises L-α-lysophosphatidylcholine as an agent for activating the immune system, which then plays the role of adjuvant, and a biological agent as defined above, against which it is desired to stimulate the patient's immune response.

According to a preferred embodiment of the invention, L-α-lysophosphatidylcholine is used as an agent for activating the immune system, for producing a medicinal product for the treatment and/or the prevention of an infection of bacterial, viral, fungal or parasitic origin or an infection caused by a yeast, and/or for the production of a medicinal product for the treatment and/or the prevention of cancers.

As bacterial infection, mention may in particular be made of infections induced by staphylococci, mycobacteria, bacteria of the *Nisseria* genus, legionellae, salmonellae, etc.

As viral infection, mention may in particular be made of infections induced by HIV (human immunodeficiency virus), hepatitis viruses, the measles virus, the rubella virus, polio viruses, flavin viruses, etc.

As fungal infection, mention may in particular be made of aspergillosis, candidosis, etc.

As parasitic infection, mention may in particular be made of malaria, leishmaniasis, etc.

The term "cancer" is intended to mean all diseases due to an abnormal multiplication of cells, and in particular, in a nonlimiting manner, melanomas, lymphomas, leukemias, kidney, brain, colon, prostate, rectal, pancreatic, ovarian, lung, liver and breast carcinomas, skin cancers chosen from keratinomas and carcinomas, and melanomas.

The medicinal product according to the invention may be provided in the form of a pharmaceutical composition in combination with at least one pharmaceutically acceptable excipient well known to those skilled in the art. In the pharmaceutical compositions according to the invention, for oral, sublingual, subcutaneous, intramuscular, intravenous, topical, intratracheal, rectal or transdermal administration, the L-α-lysophosphatidylcholine can be administered in unit administration form or as a mixture with conventional pharmaceutical supports, and when intended for oral administration, for example in the form of a tablet, a gel capsule, an oral solution, etc., or for rectal administration, in the form of a suppository, for parenteral administration, in particular in the form of an injectable solution, especially by intravenous, intradermal or subcutaneous injection, etc., according to conventional protocols well known to those skilled in the art. For topical application, the L-α-lysophosphatidylcholine can be used in creams, ointments, lotions or eye lotions.

When a solid composition is prepared in the form of tablets, the L-α-lysophosphatidylcholine is mixed with a pharmaceutically acceptable excipient, also called pharmaceutical vehicle, such as gelatin, starch, lactose, magnesium stearate, talc, gum arabic or the like. The tablets may be coated with sucrose, with a cellulose derivative or with other suitable materials. They can also be treated such that they have prolonged or delayed activity and such that they continuously release a predetermined amount of L-α-lysophosphatidylcholine. It is also possible to obtain a preparation of gel capsules by mixing the L-α-lysophosphatidylcholine with a diluent and pouring the mixture into soft or hard gel capsules. It is also possible to obtain a preparation in the form of syrup or for administration in the form of drops, in which the L-α-lysophosphatidylcholine is present together with a sweetener, an antiseptic, such as in particular methylparaben and propylparaben, and also a suitable flavor enhancer or dye. Water-dispersible powders or granules can contain the L-α-lysophosphatidylcholine as a mixture with dispersing agents or wetting agents, or suspending agents, well known to those skilled in the art. For parenteral administration, use is made of aqueous suspensions, isotonic saline solutions or sterile and injectable solutions which contain dispersing agents or wetting agents which are pharmacologically compatible, such as in particular propylene glycol or butylene glycol.

The invention also relates to the use of at least one inhibitor of L-α-lysophosphatidylcholine, for producing a medicinal product for preventing an inflammation and/or for combating an inflammatory disease and/or an autoimmune disease. The term "inhibitor of L-α-lysophosphatidylcholine" is intended to mean a molecule (or a set of molecules) which blocks the inflammatory and/or immunostimulant activity of the L-α-lysophosphatidylcholine, in particular by blocking the differentiation of mature dendritic cells by L-α-lysophosphatidylcholine. It is also intended to mean a module having effects opposite to those of L-α-lysophosphatidylcholine, by modulating in particular the PPARδ/PPARγ ratio. By way of indication, mention may be made of a lipid emulsion comprising triglycerides, phospholipids and glycerol, such as in particular INTRALIPID®, LIPOID E-80®, a PPARgamma agonist. PPARgamma agonists are well known to those skilled in the art, and mention may be made, in a nonlimiting manner, of molecules of the thiazolidinedione class, such as in particular ciglitazone, troglitazone, pioglitazone, rosiglitazone, etc. Such inhibitors could thus be used in vivo, for producing a medicinal product for decreasing an inflammatory response, in particular an inflammatory response of the joints, or especially during a transplant. According to a preferred embodiment of the invention, the inhibitor of L-α-lysophosphatidylcholine is a lipid emulsion comprising triglycerides, phospholipids and glycerol. Preferably, the triglycerides are extracted from plant oil such as in particular soybean oil. Even more preferably, the lipid emulsion comprises from 15 to 25% of soybean oil, preferably 20% of soybean oil, from 0.5 to 1.5% of egg phospholipids, preferably 1.2%, and from 1.8 to 2.6% of glycerol, preferably 2.2% of glycerol. According to another preferred embodiment of the invention, the inhibitor is a PPARgamma agonist as defined above.

As inflammatory disease, mention may be in particular be made of sarcomatosis, lupus, rheumatoid arthritis, spondylarthritis, uveitis, etc.

As autoimmune disease, mention may in particular be made of type 1 diabetes, multiple sclerosis, psoriasis, contact hypersensitivities, rheumatoid arthritis, spondylarthritis, etc.

FIG. 1 shows the titration curves giving the absorbance (Abs) as a function of the logarithm of the dilution of the serum of a batch of mice which are given LPC mixed with hen egg lysozyme (HEL, 1 mg/ml), or HEL alone.

The following examples are given by way of explanation and are in no way limiting in nature. They will make it possible to understand the invention more thoroughly.

EXAMPLE 1

Differentiation of Monocytes in Culture into Dendritic Cells in the Presence or Absence of L-α-lysophosphatidylcholine (LPC)

Isolation, placing in culture and initiation of the differentiation of monocytes—The monocytes are isolated from human peripheral blood by means of first density gradient centrifugation (620 g; 20 minutes) in Ficoll-Hypaque, followed by second centrifugation (770 g; 20 minutes) in a 50% Percoll solution. The monocytes are then purified by immunomagnetic depletion (Dynal, Oslo, Norway), using a cocktail of anti-CD19 (hydridoma 4G7) (Becton Dickinson, Francklin Lakes, N.J., USA), anti-CD3 (OKT3, American Type Culture Collection, Rockville, Md.) and anti-CD56 (NKH1, Beckman Coulter, Fullerton, Calif., USA) monoclonal antibodies. The monocytes thus obtained are then purified to at least 90%, as shown by the absence of CD1a markers and the presence of the CD14 marker. The differentiation of the monocytes into dendritic cells is initiated with 40 ng/ml of recombined human GM-CSF (Granulocyte-Macrophage Colony Stimulating Factor) and 250 U/ml of recombined human interleukin IL-4.

The monocytes are placed in culture in RPMI 1640 medium (Life Technologies, Rockeville, Md., USA) enriched with 2 mM of glutamine (Life Technologies), 10 mM of Hepes (Life Technologies), 40 ng/ml of gentamycin (Life Technologies) and 10% of lipoprotein-depleted fetal calf serum (LPDS, Sigma, St Quentin-Fallavier, France).

It should be noted that the culture medium presented in this example is an LPDS culture medium. Comparable results can be obtained using other culture media, such as an FCS medium, i.e. a medium containing 10% of non-lipoprotein-depleted fetal calf serum, or could be obtained using any synthetic culture medium known to those skilled in the art.

Treatment of the monocytes with LPC—5 days after the beginning of the differentiation of the monocytes, 40 µM of LPC (L-α-lysophosphatidylcholine; Sigma, St Quentin Fallavier, France) are added to the culture medium for 24 hours. Control cells are also obtained in the absence of LPC in the culture medium.

"Control" cells and "LPC" cells are then obtained.

EXAMPLE 2

Phenotype of Cells Obtained According to Example 1

The cells used in this analysis are those obtained on the 6th day of differentiation according to the protocol described in example 1.

The phenotype of the "control" and "LPC" cells is analyzed by flow cytometry on a FACSCalibur (Becton Dickinson, Francklin Lakes, N.J., USA) using FITC (fluorosceine isothiocyanate)-conjugated anti-CD14, anti-HLA-DR and anti-CD80 and PE (phycoerythrin)-conjugated anti-CD1a, anti-CD83, anti-CD86 and anti-CD40 (Beckman Coulter). According to the state of the art, monocytes preferentially have a CD14+ CD1a– phenotype, immature dendritic cells preferentially have a CD14– CD1a+CD86– phenotype, and mature dendritic cells preferentially have a CD14– CD1a intermediate—CD86+ phenotype.

The results obtained are given in table 1.

TABLE 1

Expression of the CD83, HLA-DR and CD86 markers in the absence (control) or in the presence of LPC

|  | CD83 | HLA-DR | CD86 |
| --- | --- | --- | --- |
| Control | 5.79 | 78.76 | 117.77 |
| LPC | 11.74 | 146.31 | 759.69 |

The "LPC" cells obtained after initiation of the differentiation of the monocytes in the presence of LPC exhibit a phenotype comparable to that of mature dendritic cells, as demonstrated in particular by the induction of CD86 markers and the increase in HLA-DR compared with the phenotype of the "control" cells.

EXAMPLE 3

Internalization Capacity of the Cells Obtained According to Example 1

The "control" and "LPC" cells used in this analysis are those obtained after 6 days of differentiation according to the protocol described in example 1. These cells are incubated at 37° C.:

for 30 minutes with 1 mg/ml of FITC-T70-Dextran (Sigma) in order to estimate the capacity of these cells for internalization by endocytosis, for 30 minutes with 1 mg/ml of Lucifer Yellow (ref. L0259, Sigma, St Quentin-Fallavier, France) in order to estimate the capacity of these cells for internalization by pinocytosis, for 3 hours with carboxylate-modified yellow-green Fluo-Spheres (trade name, 0.45 µm, Molecular Probes, Leiden, The Netherlands) in order to estimate the capacity of these cells for internalization by macropinocytosis.

The internalization is stopped on ice with a cold PBS buffer containing 0.1% of BSA (Bovine Serum Albumin) and 0.05% of $NaN_3$. The "control" and "LPC" cells are washed 3 times at 4° C. in this same buffer and the fluorescence is quantified by FACScalibur (trade name, Becton Dickinson).

As shown in table 2, the capacities for internalization by endocytosis, pinocytosis and macropinocytosis are greatly decreased by the addition of LPC to the culture medium on the 5th day of differentiation of the monocytes, compared to the control cells differentiated in the absence of LPC.

TABLE 2

Capacity for internalization by endocytosis, pinocytosis and macropinocytosis of the monocytes differentiated in the absence (control) or in the presence of LPC

|  | Endocytosis | Pinocytosis | Macropinocytosis |
|---|---|---|---|
| Control | 100% | 100% | 100% |
| LPC | 53% | 49% | 66% |

The decrease in internalization capacities is one of the characteristics of mature dendritic cells. These results show that, in the presence of LPC, the monocytes have a strong tendency to differentiate into mature dendritic cells.

EXAMPLE 4

Ability of the Cells Obtained According to Example 1 to Stimulate T Lymphocytes

The "control" and "LPC" cells used in this analysis are those obtained after 6 days of differentiation according to the protocol described in example 1.

Naïve allogenic T lymphocytes are isolated from human peripheral blood. Peripheral blood mononuclear cells are isolated by density gradient centrifugation (600 g, 20 minutes) in the presence of Ficoll-Hypaque. After elimination of the monocytes on a Percoll gradient, the peripheral blood lymphocytes are found in the dense fraction. The T lymphocytes are purified by immunomagnetic depletion using a cocktail of anti-CD19 (antibody 4G7) (Becton Dickinson, Francklin Lakes, N.J., USA), anti-CD16 (antibody 3G8), anti-CD56 (antibody NKH1), anti-glycophorin A (antibody 11E4B7.6) and anti-CD14 (antibody RMPO52), monoclonal antibodies sold by Beckman Coulter.

The purified T lymphocytes are cultured in flat-bottomed 96-well culture plates with the "control" or "LPC" cells.

$2 \times 10^5$ T cells are cultured in 200 µl of culture medium according to a monocytes differentiated in the presence or absence of LPC/T cells ratio (DC/LT ratio) of 1:5, 1:10 or 1:20. After 4 days, 50 µl of the culture supernatant are used to determine the secretion of IL-2 (interleukin 2) and of γIFN (gamma interferon) using an ELISA kit (Endogen, Woburn, Mass., USA).

As shown in table 3, the secretion of IL2 and of γIFN by the T lymphocytes, conventionally expressed according to the dendritic cells/T lymphocyte ratio (DC/LT ratio) is greatly stimulated by the cells originating from the differentiation of monocytes in the presence of LPC added 5 days after the initiation of monocyte differentiation ("LPC" cells), compared to the control results ("control" cells).

TABLE 3

Stimulation of the secretion of IL2 and of γIFN by T lymphocytes, induced by the monocytes differentiated in the absence (control) or in the presence of LPC

| DC/LT ratio |  | 0 | 0.05 | 0.1 | 0.2 |
|---|---|---|---|---|---|
| Control | IL-2 | 0 | 6 ± 8 | 15 ± 6 | 35 ± 11 |
|  | γIFN | 0 | 41 ± 14 | 51 ± 4 | 119 ± 9 |
| LPC | IL-2 | 0 | 23 ± 1 | 47 ± 26 | 173 ± 31 |
|  | γIFN | 0 | 73 ± 47 | 439 ± 108 | 795 ± 19 |

These results show an increase in the abilities of the monocytes differentiated in the presence of LPC to stimulate allogenic T lymphocytes, which is a characteristic of mature dendritic cells. By way of indication, comparable results are obtained whether the LPC is dissolved in ethanol or is in the form of a lipid emulsion.

EXAMPLE 5

Properties of the Cells Obtained According to Example 1: Comparison with Mature Dendritic Cells Obtained by Differentiation of Monocytes in the Presence of Oxidized LDLs The aim of this example is to demonstrate that the mechanisms of action involved in the differentiation of monocytes into mature dendritic cells in the presence of LPC could be different from those involved in the differentiation of monocytes into mature dendritic cells in the presence of oxidized LDLs (Perrin-Cocon et al. The Journal of Immunology, 167: 3785-3891, 2001).

In this example, the cells used are "control" and "LPC" cells as obtained in example 1, and also "LDLox" cells obtained as described in the scientific publication (Perrin-Cocon et al. The Journal of Immunology, 167: 3785-3891, 2001), i.e. after differentiation of the monocytes in culture in the presence of oxidized LDLs added to the medium 5 days after the initiation of differentiation.

The inventors investigated whether the inhibitors of the action of oxidized LDLs on the differentiation of monocytes into mature dendritic cells also inhibited the action of LPC on the differentiation of monocytes into mature dendritic cells.

Thus, a solution of INTRALIPID® (50 µg/ml of phospholipids, Fresenius Kabi, Sèvres, France), or a solution of synthetic molecules that are lipid in nature (LIPOÏD E-80®, Lipoïd Ag, Ludwigshafen, Germany, 50 µg/ml of phospholipids) was added to the culture medium on the 5th day of differentiation. The expression of CD86 by the "LPC" and "LDLox" cells in the presence of these inhibitors is analyzed according to the protocol described in example 2, and the results are given in table 4.

TABLE 4

Inhibition (in %) of the expression of CD86 by the LCP and LDLox cells, by Intralipid® and lipoïd E-80

|  | Intralipid® | Lipoïd E-80 |
|---|---|---|
| LDLox | 88% ± 10 | 81% ± 14 |
| LPC | 86% ± 12 | 24% ± 19 |

The addition of INTRALIPID® inhibits the differentiation of monocytes into mature dendritic cells by means of oxidized LDLs and by means of LPC, in a comparable manner (inhibition of the order of 80%).

On the other hand, surprisingly, the addition of LIPOÏD E-80® includes an 81% inhibition of the expression of CD86 when the monocytes are cultured in the presence of oxidized LDLs, although this inhibition is only 24% when the monocytes are cultured in the presence of LPC.

These results suggest that the mechanisms of action of LPC for the differentiation of monocytes into mature dendritic cells is different from the mechanisms of action of oxidized LDLs.

EXAMPLE 6

Cellular Mechanisms Involved in the Differentiation of Monocytes into Mature Dendritic Cells in the Presence of LPC In order to advance further in the search for the cellular mechanisms of the action of LPC in the differentiation of monocytes into mature dendritic cells, the inventors investigated which receptors could be involved.

Initially, in order to determine whether the receptors involved in the action of LPC in the differentiation of monocytes into mature dendritic cells belonged to the family of G protein-coupled receptors, PTX (pertussis toxin; 100 ng/ml), known to block Gi proteins, was added to the culture medium for 3 hours. The culture medium was then changed and the LPC was added as described in example 1.

The results given in table 5 show that preincubation of the monocytes with PTX blocks the increase in CD86 induced by LPC, suggesting that the action of LPC involves Gi protein-coupled receptors.

TABLE 5

Inhibition of the expression of CD86 by the "LPC" cells, with PTX

|  | Induction of CD86 |
|---|---|
| LPC | 100% |
| LPC + PTX | 10% |

These receptors could in particular be the following receptors:

G2A receptor (G2A-R): it has recently been demonstrated that LPC is a high-affinity ligand for the G2A protein, a G protein coupled to a receptor expressed in lymphocytes. In addition, the stimulation of G2A by LPC induces phosphorylation of an extracellular kinase (ERK1/2: extracellular signal-related kinases). This phosphorylation can, moreover, be observed when LPC is added to the culture medium, suggesting the involvement of the G2A receptor in the differentiation of monocytes into mature dendritic cells by means of LPC, PAF receptor (PAF-R) as described above; certain effects of LPC could involve the PAF receptor in various types of cells, GPR4 receptor: LPC is also a ligand for the GPR4 protein, another G protein coupled to a receptor having a high affinity for sphingosylphosphorylcholine.

Next, the inventors investigated the transcription factors involved in the maturation process induced by LPC. In order to determine whether PPARs are involved in the LPC-induced maturation, the ability of the two transcription factors PPARγ and PPARδ to bind was analyzed using the gel shift technique. 3 isotypes of PPAR nuclear receptors (peroxisome proliferator-activated receptor) exist: α, γ and δ. PPARγs are the targets for molecules of the thiazolidinedione class, such as ciglitizone, used in the treatment of type II diabetes. PPARδs have a broader expression and can be repressors of PPARγs. The monocytes undergoing differentiation were incubated for two hours with a solution of LPC (40 µM) ("LPC" cells). "Control" cells are also obtained in the absence of LPC in the culture medium. After having harvested the cells, the nuclear proteins were extracted with the Nuclear extract Kit (Sigma). The nuclear proteins were then brought into contact with a ratioactively labeled probe containing a response element recognized by PPARs. After migration on a nondenaturing gel, a band containing PPARγ and a doublet containing PPARδ were identified using antibodies, by the Supershift technique. The PPAR binding activity was determined by measuring the intensity of these bands. These activities are expressed as a percentage with respect to the "control" cells.

TABLE 6

Modulation of the activity of PPARγ and PPARδ by LPC

|  | PPARγ | PPARδ |
|---|---|---|
| Control | 100% | 100% |
| LPC | 0% | 263% |

The treatment with LPC induces a large decrease in the binding activity of PPARγ, which can result in complete disappearance, and greatly stimulates the activity of PPARδ.

The inventors then used a PPARγ agonist, ciglitizone. A solution of ciglitizone (Sigma, 50 µM) was added to the culture medium on the fifth day of monocyte differentiation, as described in example 1, 15 minutes before the addition of a solution of LPC (40 µM, for 2 hours). The cells obtained are "LPC+ciglitizone" cells. "Ciglitizone" cells were obtained according to the same protocol, but in the absence of LPC, and "LPC" cells were obtained as described in example 1, in the absence of ciglitizone.

The activity of the PPARγ and PPARδ transcription factors was measured in these cells by the gel shift technique, as described above.

TABLE 7

Ciglitizone blocks the inactivation of PPARγ and reduces the LPC-induced increase in PPARδ

|  | PPARγ | PPARδ |
|---|---|---|
| Control | 100% | 100% |
| Ciglitizone | 237% | 106% |
| LPC + ciglitizone | 115% | 147% |

These results indicate that ciglitizone, which activates PPARγ, greatly inhibits the effect of LPC on PPARγ and PPARδ, and as a result blocks the LPC-induced maturation of dendritic cells.

The functional ability of these cells ("control", "ciglitazone" and "LPC+ciglitazone" cells) to stimulate T lymphocytes (LT) were then analyzed. These cells were cultured as described in example 4, in the presence of purified allogenic T lymphocytes. The secretion of γIFN was measured as in example 4.

TABLE 8

Mixed leukocyte reaction: measurement of the dendritic cell-induced secretion of γIFN by T lymphocytes

| DC/LT ratio | 0 | 0.05 | 0.1 | 0.2 |
|---|---|---|---|---|
| Control | 0 | 54 ± 82 | 69 ± 4 | 364 ± 27 |
| LPC | 0 | 750 ± 184 | 899 ± 124 | 1326 ± 248 |
| LPC + ciglitizone | 0 | 93 ± 7 | 169 ± 105 | 484 ± 229 |

All these results emphasize an important role for PPARs in the LPC-induced maturation of dendritic cells and also the importance of the PPARγ/PPARδ ratio in the production of functionally mature dendritic cells. This ratio is modulated by LPC and ciglitizone.

EXAMPLE 7

Differentiation of Monocytes into Mature Dendritic Cells in the Presence of Compounds Equivalent to LPC The inventors determined whether compounds equivalent to LPC, i.e. involving the same cellular mechanisms of action via the same membrane or intracellular receptors, could also induce the differentiation of monocytes into mature dendritic cells.

For this, the inventors investigated whether the addition of PAF to the culture medium could increase the action of LPC on the differentiation of monocytes into mature dendritic cells.

Thus, a solution of PAF (Sigma, 5 μM) was added to the culture medium on the 5th day of monocyte differentiation. The expression of CD86 by the "control" cells and by the "LPC" cells, obtained in the presence or in the absence of PAF, was analyzed according to the protocol described in example 2, and the results are given in table 9.

TABLE 9

Expression of the CD86 marker (mean fluorescence intensity) by the "control" and "LPC" cells in the presence or in the absence of PAF

| | CD86 |
|---|---|
| Control | 49.02 |
| PAF | 102.88 |
| LPC | 287.11 |
| LPC + PAF | 676.88 |

These results suggest that PAF alone induces a slight overexpression of CD86, unlike LPC, which induces a 470% increase in the expression of CD86. On the other hand, it is important to note that PAF acts in synergy with LPC, since the action of the two compounds induces a 1200% increase in the expression of CD86.

In order to reinforce the idea that the PAF receptor is involved, the inventors studied the action of an antagonist for this receptor on the differentiation of monocytes into mature dendritic cells by means of LPC.

Thus, a solution of the PAF antagonist BN52021 (Biomol, Plymouth Meeting, USA, 100 μM) was added to the culture medium on the 5th day of monocyte differentiation. The expression of CD86 by the "control" and "LPC" cells, obtained in the presence or in the absence of BN52021, was analyzed according to the protocol described in example 2, and the results are given in table 10.

TABLE 10

Expression of CD86 by the "LPC" cells in the presence of the antagonist BN52021

| | CD86 |
|---|---|
| LPC | 100% |
| LPC + BN52021 | 54% |

These results suggest that the action of LPC clearly involves the PAF receptor, but also suggest that the action of LPC could involve other receptors.

By way of indication, the inventors also demonstrated that the antagonist BN52021, added to the culture medium on the 5th day of differentiation of the monocytes into mature dendritic cells induced by oxidized LDLs, induced a 100% inhibition of the action of the oxidized LDLs, suggesting here again that the mechanisms of action of LPC and of oxidized LDLs are different.

EXAMPLE 8

In Vivo Stimulation of the Immune Response Against an Antigen, by LPC

The aim of this example is to show that LPC is a molecule which is an adjuvant of the immune system and which can be used in the context of immunization in order to increase the specific T response against an antigen.

LPC is an inflammatory product—In this example, a solution of 100 to 500 nmol of LPC dissolved in 50 μl of PBS is injected into the plantar foot pad of BALB/c mice (Charles River Laboratories) on day 0. The plantar foot pads are measured using a micrometer before and after injection, up to the 10th day, and compared to the plantar foot pads of "control" mice, obtained by injection of PBS (50 μl). The intensity of the inflammation is reflected by the thickening of the foot. The maximum thickening is observed on the 1st day, 24 h after the injection.

TABLE 11

Inflammation of the plantar foot pad induced by LPC-thickening of the foot after 24 h (in mm)

| | Thickening of the foot (mm) |
|---|---|
| PBS | 0.025 |
| LPC 100 nmol | 0.35 |
| LPC 200 nmol | 0.55 |
| LPC 300 nmol | 0.725 |
| LPC 400 nmol | 1.125 |
| LPC 500 nmol | 1.075 |

These results show that LPC induces an inflammation dependent on the dose injected.

In order to show that LPC induces the maturation and therefore the migration of dendritic cells to the draining lymph nodes, in vivo, a solution of LPC (0.1 M in dibutyl phthalate) was applied to the skin of the ears of BALB/c mice (Charles River Laboratories), 10 minutes before application of a solution of FITC (Sigma) at 1.5% in 1:1 dibutyl phthalate/acetone. This fluorescent label is taken up by the dendritic cells of the skin. After 24 h, the auricular and maxillary lymph nodes are removed and the cells are placed in suspension. The cell suspension is enriched in dendritic cells by metrizamide (Sigma) gradient centrifugation. The cells are labeled with an antibody (Pharmingen) which recognizes Major Histocompatibility Complex (MHC) class I molecules and analysis by flow cytometry makes it possible to quantify the percentage of large cells (dendritic cells) expressing the MHC class II molecules and containing FITC. These cells are presenting cells which have taken up the FITC in the periphery and have migrated to the lymph nodes.

TABLE 12

Stimulation of dendritic cell migration by LPC

| | FITC+ dendritic cells |
|---|---|
| FITC | 7.1 ± 1.7% |
| LPC + FITC | 19.3 ± 3.3% |

These results show that the application of LPC stimulates the migration of dendritic cells of the skin to the draining lymph nodes.

LPC stimulates the T response specific for a co-injected soluble antigen. LPC dissolved in PBS (250 or 500 nmol in 50 μl) is mixed with hen egg lysozyme (HEL, 50 μg) and this mixture is injected into the plantar foot pad of BALB/c mice. After 7 days, the popliteal lymph nodes are removed and their cells are restimulated in triplicate in vitro, in a culture medium containing 30 μM of HEL antigen, or in the absence of HEL. After 3 days, the T lymphocyte proliferation is measured by incorporation of triturated thymidine for 16 h.

TABLE 13

Proliferation of HEL-specific T cells
(incorporation of triturated thymidine in CPM; mean of triplicates)

| Immunization conditions | Proliferation in the absence of HEL | Restimulation with HEL (30 μM) |
|---|---|---|
| HEL | 1315 ± 275 | 5370 ± 1983 |
| HEL + LPC 250 nmol | 1608 ± 7 | 10885 ± 2861 |
| HEL + LPC 500 nmol | 2101 ± 87 | 23739 ± 4265 |

These results show that LPC co-injected with the antigen promotes the activation in vivo of T lymphocytes specific for this antigen.

LPC stimulates the production of specific antibodies against a co-injected soluble antigen. LPC dissolved in PBS (350 nmol in 50 μl) is mixed with hen egg lysozyme (HEL, 1 mg/ml) and this mixture is injected into the plantar foot pad of BALB/c mice. The "HEL+LPC" batch of mice receives 50 μl of this mixture in the foot pads of the two hind feet. The "HEL" batch of mice receives 50 μl of HEL solution (1 mg/ml in PBS) in the two feet. After 15 days, a booster injection is given subcutaneously on the 2 flanks. The "HEL+LPC" batch receives, on each flank, 100 μl of a solution of LPC (5 mM) and of HEL (1 mg/ml) in PBS. The "HEL" batch receives, on each flank, 100 μl of a solution of HEL (1 mg/ml) in PBS. Two weeks later, blood is taken from the mice and the IgGs specific for the HEL antigen are assayed by ELISA with respect to a standard IgG solution range. The titration curves giving the absorbance (Abs) as a function of the logarithm of the serum dilution are represented in FIG. 1.

These results suggest that LPC co-injected with the antigen promotes activation of the immune system and induces the synthesis of antibodies specific for the antigen, whereas injection of the antigen alone does not induce a response. LPC induces a humoral response against the antigen, demonstrating its adjuvant capacity.

LPC can induce a CD8+ T lymphocyte response in vivo. In this example, a test for delayed contact hypersensitivity to haptens was used. In this model, BALB/c mice are sensitized by application of a hapten, DNFB (1-fluoro-2,4-dinitrobenzene, 0.5% solution in 1:1 olive oil/acetone), to the back. Five days later, a non-irritant dose of DNFB (0.2% solution in 1:1 olive oil/acetone) is applied to the left ear, whereas the right ear receives the solvent. In this elicitation phase, CD8+ T lymphocytes specific for the haptenized proteins are recruited and infiltrate the ear, secreting γIFN and producing an edema.

A "control" batch of mice was sensitized with DNFB alone and another batch ("LPC" mice) received 500 nmol of LPC by application to the skin of the back of 20 μl of an ethanolic solution of LPC, 10 minutes before the application of DNFB. Five days later, the two batches were treated in the same way for the elicitation phase and the thickening of the ears was measured using a micrometer 48 h after this application.

TABLE 14

Measurement of the ear edema

| | Thickening of the right ear (μm) | Thickening of the left ear (μm) |
|---|---|---|
| Control | 0 ± 4 | 67 ± 32 |
| LPC | 0 ± 3 | 149 ± 31 |

These results show that the application of LPC 10 minutes before the hapten during the sensitization phase increases the edema induced during the 2nd application of the hapten (elicitation). This means that LPC stimulates the response relayed by CD8+ T lymphocytes.

EXAMPLE 9

Action of a Lipid Emulsion Such as INTRALIPID® on the Differentiation of Monocytes into Mature Dendritic Cells Since it was shown in example 5 that a lipid emulsion such as INTRALIPID® blocks the LPC-induced production of mature dendritic cells, the inventors also investigated whether this blocking came from an indirect action of this lipid emulsion via inhibition of the action of LPC and/or from a direct action of this lipid emulsion.

INTRALIPID® regulates PPARs in vitro. Initially, a solution of INTRALIPID® (50 μg/ml of phospholipids) was added to the culture medium on the 5th day of monocyte differentiation, according to a protocol comparable to that described in example 6. The cells were harvested after 1 h, 2 h or 8 h of incubation with INTRALIPID®, the nuclear proteins were extracted and the activity of PPARγ and PPARδ was determined as described in example 6.

TABLE 15

Modulation of the activity of PPARγ and PPARδ
of monocytes undergoing differentiation, by Intralipid ®

| Incubation time with Intralipid (h) | PPARγ | PPARδ |
|---|---|---|
| 0 | 100% | 100% |
| 1 | 130% | 94% |
| 2 | 160% | 94% |
| 8 | 170% | 77% |

These results show that INTRALIPID® alone activates PPARγ and inhibits the activity of PPARδ. This action of INTRALIPID® is opposite to that of LPC.

Secondly, a solution of INTRALIPID® (50 μg/ml of phospholipids) was added to the culture medium on the 5th day of monocyte differentiation, 15 minutes before the addition of a solution of LPC (40 μM) ("LPC+Intralipid" cells). "Intralipid" cells were also obtained in the absence of LPC. "LPC" cells were obtained in the absence of INTRALIPID®. The cells were harvested after 2 h of incubation, the nuclear proteins were extracted and the activity of PPARγ and PPARδ was determined as described in example 6.

TABLE 16

Intralipid ® blocks the LPC-induced generation
of mature dendritic cells by modulating the activity of
PPARγ and PPARδ

|  | PPARγ | PPARδ |
|---|---|---|
| Control | 100% | 100% |
| Intralipid | 156% | 99% |
| LPC | 1% | 160% |
| LPC + Intralipid | 40% | 80% |

INTRALIPID® also blocks the action of LPC by modulating the activity of PPARγ and PPARδ.

INTRALIPID® blocks the inflammation and the immune response induced by LPC, in vivo. In this example, 3 batches of BALB/c mice are immunized against the hen egg lysozyme (HEL) antigen by injection of 50 μl of solution into the plantar foot pad. The "HEL" control batch receives 50 μg of HEL, the "HEL+Intralipid" batch receives a mixture of INTRALIPID® (45 μl) and of 50 μg of HEL (5 μl of a solution at 10 mg/ml). The "HEL+LPC" batch receives 50 μg of HEL with 350 nmol of LPC dissolved in PBS. The "HEL+LPC+Intralipid" batch receives 50 μg of HEL mixed with 350 nmol of LPC dissolved in 45 μl of INTRALIPID®. After 24 hours, the thickness of the foot pads is measured using a micrometer, and compared with the measurement taken before injection. The difference in thickness is proportional to the intensity of the inflammation.

TABLE 17

Intralipid reduces the inflammation induced in
vivo by LPC

|  | Average thickness of the foot at 24 h (mm) |
|---|---|
| HEL + Intralipid | 0.19 ± 0.04 |
| HEL + LPC | 1.07 ± 0.19 |
| HEL + LPC + Intralipid | 0.45 ± 0.04 |

These results show that injecting INTRALIPID® at the same time as LPC reduces the LPC-induced inflammation of the plantar foot pad by 70%.

Seven days after the injection, the popliteal lymph nodes are removed and their cells are restimulated in vitro in triplicate, in a culture medium containing 10 μM of HEL or in the absence of HEL. After 3 days, the proliferation of HEL-specific T lymphocytes is measured by incorporation of triturated thymidine for 16 h.

TABLE 18

Proliferation of HEL-specific T cells (mean of the mice)

| Immunization conditions | Proliferation in the absence of HEL (cpm) | Restimulation with HEL (10 μM) (cpm) |
|---|---|---|
| HEL | 370 ± 212 | 738 ± 408 |
| HEL + LPC | 2568 ± 1570 | 11340 ± 4426 |
| HEL + LPC + Intralipid | 1124 ± 541 | 3959 ± 2103 |

These results show that INTRALIPID® injected at the same time as LPC blocks the LPC-induced stimulation of the T response.

All these results show that INTRALIPID® blocks the LPC-induced generation of mature dendritic cells by means of an indirect action of INTRALIPID® via inhibition of the action of LPC, but also by means of a direct action of INTRALIPID® on PPARs, antagonist for LPC. These results show that INTRALIPID® alone has an anti-inflammatory role.

All these results show the importance of the PPARγ/PPARδ ratio in the generation of functionally mature dendritic cells. This ratio is modulated by LPC, but also, inversely, by a lipid emulsion such as INTRALIPID® or ciglitizone.

The invention claimed is:
1. A method for the differentiation in vitro of monocytes into mature dendritic cells, according to which:
   (a) monocytes are provided in a suitable culture medium,
   (b) the differentiation of the monocytes into dendritic cells is induced in the presence of GM-CSF and IL-4;
   (c) a molecule consisting of L-α-lysophosphatidylcholine (LPC) is added to said medium; and
   (d) mature dendritic cells are obtained.
2. The method as claimed in claim 1, according to which, in step (c), the L-α-lysophosphatidylcholine is added to said medium at a final concentration in the medium of between 10 and 80 μM.
3. The method as claimed in claim 1, according to which, in step (c), the L-α-lysophosphatidylcholine is added to said medium between the 3rd and 6th day of monocyte differentiation.
4. The method as claimed in claim 1, wherein, in step (c), at least one biological agent is also added to the culture medium, wherein the biological agent is a bacterial, viral, yeast, parasite or fungal antigen, an autologous and/or heterologous tumor cell lystate antigen, a tumor antigen, a nucleic acid which encodes a bacterial, viral, yeast, parasite or fungal antigen, or nucleic acid which encodes a tumor antigen.
5. The method as claimed in claim 1, wherein, in step (c), a platelet activating factor (PAF) is also added to the culture medium.

* * * * *